United States Patent
Wong et al.

(10) Patent No.: US 10,919,037 B2
(45) Date of Patent: Feb. 16, 2021

(54) SYSTEMS AND APPARATUS FOR DETECTING COMPOUNDS IN HUMAN BIOLOGICAL SAMPLES

(71) Applicant: Children's Medical Center Corporation, Boston, MA (US)

(72) Inventors: Wesley Philip Wong, Cambridge, MA (US); Clinton H. Hansen, Cambridge, MA (US); Mounir Ahmad Koussa, Somerville, MA (US)

(73) Assignee: Children's Medical Center Corporation, Boston, MA (US)

(*) Notice: Subject to any disclaimer, the term of this patent is extended or adjusted under 35 U.S.C. 154(b) by 200 days.

(21) Appl. No.: 16/087,500

(22) PCT Filed: Mar. 23, 2017

(86) PCT No.: PCT/US2017/023711
§ 371 (c)(1),
(2) Date: Sep. 21, 2018

(87) PCT Pub. No.: WO2017/165585
PCT Pub. Date: Sep. 28, 2017

(65) Prior Publication Data
US 2019/0070604 A1  Mar. 7, 2019

Related U.S. Application Data

(60) Provisional application No. 62/311,977, filed on Mar. 23, 2016.

(51) Int. Cl.
*G01N 27/453* (2006.01)
*B01L 3/00* (2006.01)
(Continued)

(52) U.S. Cl.
CPC .. *B01L 3/502715* (2013.01); *G01N 27/44704* (2013.01); *G01N 27/44743* (2013.01);
(Continued)

(58) Field of Classification Search
CPC ....... G01N 27/44743; G01N 27/44756; G01N 27/44791
See application file for complete search history.

(56) References Cited

U.S. PATENT DOCUMENTS

| | | | |
|---|---|---|---|
| 5,571,677 A | 11/1996 | Gryaznov | |
| 5,635,352 A | 6/1997 | Urdea et al. | |

(Continued)

FOREIGN PATENT DOCUMENTS

| | | |
|---|---|---|
| JP | H06-508753 A | 10/1994 |
| JP | 2000-312589 A | 8/2000 |

(Continued)

OTHER PUBLICATIONS

Yang et al., "An integratable microfluidic cartridge for forensic swab samples lysis," Forensic Science International: Genetics 8 (2014) 147-158 (Year: 2014).*

(Continued)

*Primary Examiner* — Alexander S Noguerola
(74) *Attorney, Agent, or Firm* — Wolf, Greenfield & Sacks, P.C.

(57) ABSTRACT

Systems and apparatus for performing analysis of human biological samples are described. Collected biological samples are combined with a substance including nucleic acid complexes and the combined substance is processed using gel electrophoresis. An indication of a detected compound in the biological sample and/or a particular medical condition associated with the detected compound is output from the apparatus.

19 Claims, 8 Drawing Sheets

(51) Int. Cl.
  *G01N 27/447* (2006.01)
  *G01N 33/487* (2006.01)
  *G01N 33/561* (2006.01)
(52) U.S. Cl.
  CPC ..... *G01N 33/48707* (2013.01); *G01N 33/561* (2013.01); *B01L 2200/027* (2013.01); *B01L 2200/10* (2013.01); *B01L 2300/023* (2013.01); *B01L 2300/027* (2013.01); *B01L 2300/069* (2013.01); *B01L 2400/0421* (2013.01); *G01N 27/44756* (2013.01)

(56) References Cited

U.S. PATENT DOCUMENTS

| | | | |
|---|---|---|---|
| 5,902,724 | A | 5/1999 | Lane et al. |
| 6,251,660 | B1 | 6/2001 | Muir et al. |
| 6,770,698 | B1 * | 8/2004 | Chu ............ C08F 271/00 524/458 |
| 8,491,454 | B2 | 7/2013 | Wong et al. |
| 8,795,143 | B2 | 8/2014 | Wong et al. |
| 9,255,905 | B1 * | 2/2016 | Mellors ............ B01L 3/50273 |
| 9,914,958 | B2 | 3/2018 | Wong et al. |
| 9,994,839 | B2 * | 6/2018 | Lo ............ C12N 15/1003 |
| 2002/0177144 | A1 | 11/2002 | Remacle et al. |
| 2003/0143549 | A1 | 7/2003 | Yang et al. |
| 2007/0117109 | A1 | 5/2007 | Rothemund |
| 2007/0154899 | A1 | 7/2007 | Coull et al. |
| 2007/0155017 | A1 | 7/2007 | Wyatt |
| 2008/0312103 | A1 | 12/2008 | Nemoto et al. |
| 2009/0087838 | A1 | 4/2009 | Reif et al. |
| 2009/0286694 | A1 | 11/2009 | Zainiev et al. |
| 2010/0015608 | A1 | 1/2010 | Kolpashchikov |
| 2010/0035247 | A1 | 2/2010 | Burton |
| 2010/0137120 | A1 | 6/2010 | Wong et al. |
| 2010/0206730 | A1 | 8/2010 | Hunkapiller et al. |
| 2010/0216658 | A1 | 8/2010 | Chaput et al. |
| 2011/0086774 | A1 | 4/2011 | Dunaway |
| 2011/0268654 | A1 | 11/2011 | Hilderbrand et al. |
| 2012/0058008 | A1 | 3/2012 | Corbett et al. |
| 2013/0004523 | A1 | 1/2013 | Zubarev et al. |
| 2013/0130884 | A1 | 5/2013 | Wong et al. |
| 2013/0196341 | A1 | 8/2013 | Neely et al. |
| 2013/0225429 | A1 | 8/2013 | Curry |
| 2013/0310260 | A1 | 11/2013 | Kim et al. |
| 2013/0344508 | A1 | 12/2013 | Schwartz et al. |
| 2014/0255939 | A1 | 9/2014 | Wong et al. |
| 2014/0284213 | A1 | 9/2014 | Sabin et al. |
| 2015/0027894 | A1 | 1/2015 | Puleo et al. |
| 2015/0099650 | A1 | 4/2015 | Sood et al. |
| 2015/0361422 | A1 | 12/2015 | Sampson et al. |
| 2017/0369935 | A1 | 12/2017 | Koussa et al. |
| 2018/0135043 | A1 | 5/2018 | Wong et al. |
| 2018/0223344 | A1 | 8/2018 | Chandrasekaran et al. |
| 2018/0291434 | A1 | 10/2018 | Wong et al. |
| 2019/0048409 | A1 | 2/2019 | Wong et al. |
| 2019/0064056 | A1 | 2/2019 | Yang et al. |

FOREIGN PATENT DOCUMENTS

| | | |
|---|---|---|
| JP | 2003-219897 A | 8/2003 |
| JP | 2005-536234 A | 12/2005 |
| JP | 2008-259453 A | 10/2008 |
| JP | 2009-521230 | 6/2009 |
| WO | WO 93/01313 A1 | 1/1993 |
| WO | WO 98/18961 A1 | 5/1998 |
| WO | WO 00/40751 A2 | 7/2000 |
| WO | WO 2004/016767 A2 | 2/2004 |
| WO | WO 2007/076128 A2 | 7/2007 |
| WO | WO 2011/005221 A1 | 1/2011 |
| WO | WO 2011/153211 A1 | 12/2011 |
| WO | WO 2012/058638 A2 | 5/2012 |
| WO | WO 2013/010023 A2 | 1/2013 |
| WO | WO 2014/011800 A1 | 1/2014 |
| WO | WO 2015/006626 A1 | 1/2015 |
| WO | WO 2015040009 A1 * | 3/2015 ............ B01L 3/00 |
| WO | WO 2016/089588 A1 | 6/2016 |
| WO | WO 2017/003950 A2 | 1/2017 |

OTHER PUBLICATIONS

Hopwood et al., "Integrated Microfluidic System for Rapid Forensic DNA Analysis: Sample Collection to DNA Profile," Anal. Chem. 2010, 82, 6991-6999 (Year: 2010).*
Invitation to Pay Additional Fees for International Application No. PCT/US2017/023711 mailed May 5, 2017.
International Search Report and Written Opinion for International Application No. PCT/US2017/023711 dated Jul. 6, 2017.
International Preliminary Report on Patentability for International Application No. PCT/US2017/023711 dated Oct. 4, 2018.
[No Author Listed], Wikipedia Entry, "Xhol." May 14, 2014. Retrieved from the internet. <https://en.wikipedia.org/w/index/php?title=Xhol&oldid=608536958>. Retrieved on Oct. 18, 2016.
Aaij et al., The gel electrophoresis of DNA. Biochim Biophys Acta. May 10, 1972;269(2):192-200.
Baumann et al., Ionic effects on the elasticity of single DNA molecules. Proc Natl Acad Sci U S A. Jun. 10, 1997;94(12):6185-90.
Bellot et al., Recovery of intact DNA nanostructures after agarose gel-based separation. Nat Methods. Mar. 2011;8(3):192-4. doi: 10.1038/nmeth0311-192.
Bishop et al., Electrophoretic separation of viral nucleic acids on polyacrylamide gels. J Mol Biol. Jun. 28, 1967;26(3):373-87.
Bustamante et al., Entropic elasticity of lambda-phage DNA. Science. Sep. 9, 1994;265(5178):1599-600.
Bustamante et al., Ten years of tension: single-molecule DNA mechanics. Nature. Jan. 23, 2003;421(6921):423-7.
Chandrasekaran et al., Label-free Detection of Specific Nucleic Acid Sequences using DNA Nanoswitches. The RNA Institute , University at Albany, State University of New York.
Chandrasekaran et al., Programmable DNA Nanoswitches for Detection of Nucleic Acid Sequences. ACS Sens., 2016, 1 (2), pp. 120-123.
Cheng et al., Early pregnancy factor in cervical mucus of pregnant women. Am J Reprod Immunol. Feb. 2004;51(2):102-5.
Chilkoti et al., Molecular Origins of the Slow Streptavidin-Biotin Dissociation Kinetics. J Am Chem Soc. 1995;117(43):10622-8.
Chivers et al., A streptavidin variant with slower biotin dissociation and increased mechanostability. Nat Methods. May 2010;7(5):391-3. doi: 10.1038/nmeth.1450. Epub Apr. 11, 2010.
Cho et al., A genomic-scale view of the cAMP response element-enhancer decoy: a tumor target-based genetic tool. Proc Natl Acad Sci U S A. Nov. 26, 2002;99(24):15626-31. Epub Nov. 18, 2002.
Conde et al., Implantable hydrogel embedded dark-gold nanoswitch as a theranostic probe to sense and overcome cancer multidrug resistance. Proc Natl Acad Sci U S A. Mar. 17, 2015;112(11):E1278-87. doi: 10.1073/pnas.1421229112. Epub Mar. 2, 2015.
Deniz et al., Single-molecule biophysics: at the interface of biology, physics and chemistry. J R Soc Interface. Jan. 6, 2008;5(18):15-45.
Doshi et al., In vitro nanobody discovery for integral membrane protein targets. Sci Rep. Oct. 24, 2014;4:6760. doi: 10.1038/srep06760.
Douglas et al., A logic-gated nanorobot for targeted transport of molecular payloads. Science. Feb. 17, 2012;335(6070):831-4. doi: 10.1126/science.1214081.
Douglas et al., Self-assembly of DNA into nanoscale three-dimensional shapes. Nature. May 21, 2009;459(7245):414-8. doi: 10.1038/nature08016.
Evans et al., Dynamic strength of molecular adhesion bonds. Biophys J. Apr. 1997;72(4):1541-55.
Evans et al., Forces and bond dynamics in cell adhesion. Science. May 25, 2007;316(5828):1148-53.
Evans, Probing the relation between force—lifetime—and chemistry in single molecular bonds. Annu Rev Biophys Biomol Struct. 2001;30:105-28.

(56) References Cited

OTHER PUBLICATIONS

Fazio et al., DNA curtains and nanoscale curtain rods: high-throughput tools for single molecule imaging. Langmuir. Sep. 16, 2008;24(18):10524-31. doi: 10.1021/la801762h. Epub Aug. 7, 2008.
França et al., A review of DNA sequencing techniques. Q Rev Biophys. May 2002;35(2):169-200.
Green, Avidin and streptavidin. Methods Enzymol. 1990;184:51-67.
Greenleaf et al., High-resolution, single-molecule measurements of biomolecular motion. Annu Rev Biophys Biomol Struct. 2007;36:171-90.
Halvorsen et al., Binary DNA nanostructures for data encryption. PLoS One. 2012;7(9):e44212. doi: 10.1371/journal.pone.0044212. Epub Sep. 11, 2012.
Halvorsen et al., Cross-platform comparison of nucleic acid hybridization: toward quantitative reference standards. Anal Biochem. Nov. 15, 2014;465:127-33. doi: 10.1016/j.ab.2014.08.001. Epub Aug. 12, 2014.
Halvorsen et al., Massively Parallel Single-Molecule Manipulation Using Centrifugal Force. Biophys J. Jun. 2, 2010;98(11):L53-5.
Halvorsen et al., Nanoengineering a single-molecule mechanical switch using DNA self-assembly. Nanotechnology. Dec. 9, 2011;22(49):494005. doi:10.1088/0957-4484/22/49/494005. Epub Nov. 21, 2011.
Halvorsen, Probing Weak Single-Molecule Interactions: Development and Demonstration of a New Instrument. Boston University, College of Engineering dissertation. 2007: 102 pages.
Hanke et al., Entropy loss in long-distance DNA looping. Biophys J. Jul. 2003;85(1):167-73.
Hansen et al., Nanoswitch-linked immunosorbent assay (NLISA) for fast, sensitive, and specific protein detection. PNAS. Sep. 26, 2017;114(39):10367-10372. Supporting Information, 4 pages.
Hassur et al., UV shadowing—a new and convenient method for the location of ultraviolet-absorbing species in polyacrylamide gels. Anal Biochem. May 1974;59(1):162-4.
Hellman et al., Electrophoretic mobility shift assay (EMSA) for detecting protein-nucleic acid interactions. Nat Protoc. 2007;2(8):1849-61.
Idili et al., Programmable pH-triggered DNA nanoswitches. J Am Chem Soc. Apr. 23, 2014;136(16):5836-9. doi: 10.1021/ja500619w. Epub Apr. 9, 2014. Abstract only.
Jones et al, Nanomaterials. Programmable materials and the nature of the DNA bond. Science. Feb. 20, 2015;347(6224):1260901. doi: 10.1126/science.1260901.
Jung et al., Binding and Dissociation Kinetics of Wild-Type and Mutant Streptavidins on Mixed Biotin-Containing Alkylthiolate Monolayers. Langmuir. Nov. 28, 2000;16(24): 9421-32.
Khalil et al., Single M13 bacteriophage tethering and stretching. Proc Natl Acad Sci U S A. Mar. 20, 2007;104(12):4892-7. Epub Mar. 13, 2007.
Kim et al., A mechanically stabilized receptor-ligand flex-bond important in the vasculature. Nature. Aug. 19, 2010;466(7309):992-5. doi: 10.1038/nature09295.
Kim et al., Multiplexed single-molecule assay for enzymatic activity on flow-stretched DNA. Nat Methods. May 2007;4(5):397-9. Epub Apr. 15, 2007.
Klumb et al., Energetic roles of hydrogen bonds at the ureido oxygen binding pocket in the streptavidin-biotin complex. Biochemistry. May 26, 1998;37(21):7657-63.
Koch et al., Prospects and limitations of the rosette inhibition test to detect activity of early pregnancy factor in the pig. J Reprod Fertil. May 1985;74(1):29-38.
Koussa et al., DNA nanoswitches: a quantitative platform for gel-based biomolecular interaction analysis. Nat Methods. Feb. 2015;12(2):123-6. doi: 10.1038/nmeth.3209. Epub Dec. 8, 2014.
Koussa et al., Protocol for sortase-mediated construction of DNA-protein hybrids and functional nanostructures. Methods. May 15, 2014;67(2):134-41. doi: 10.1016/j.ymeth.2014.02.020. Epub Feb. 22, 2014.
Kufer et al., Single-molecule cut-and-paste surface assembly. Science. Feb. 1, 2008;319(5863):594-6. doi:10.1126/science.1151424.
Leier et al., Cryptography with DNA binary strands. Biosystems. Jun. 2000;57(1):13-22.
Mcdonell et al., Analysis of restriction fragments of T7 DNA and determination of molecular weights by electrophoresis in neutral and alkaline gels. J Mol Biol. Feb. 15, 1977;110(1):119-46.
Modi et al., A DNA nanomachine that maps spatial and temporal pH changes inside living cells. Nat Nanotechnol. May 2009;4(5):325-30. doi: 10.1038/nnano.2009.83. Epub Apr. 6, 2009. Abstract only.
Morton et al., Rosette inhibition test: A multicentre investigation of early pregnancy factor in humans. J Reprod Immunol. Sep. 1982;4(5):251-61.
Morton et al., Early pregnancy factor. Semin Reprod Endocrinol. May 1992;10:72-82.
Nelson et al., Tethered particle motion as a diagnostic of DNA tether length. J Phys Chem B. Aug. 31, 2006;110(34):17260-7. Abstract only.
Neuman et al., Single-molecule force spectroscopy: optical tweezers, magnetic tweezers and atomic force microscopy. Nat Methods. Jun. 2008;5(6):491-505. doi: 10.1038/nmeth.1218.
Park et al., Dual blockade of cyclic AMP response element- (CRE) and AP-1-directed transcription by CRE-transcription factor decoy oligonucleotide. gene-specific inhibition of tumor growth. J Biol Chem. Jan. 15, 1999;274(3):1573-80.
Pei et al, A DNA nanostructure-based biomolecular probe carrier platform for electrochemical biosensing. Adv Mater. Nov. 9, 2010;22(42):4754-8. doi: 10.1002/adma.201002767.
Quek et al., Mechanically controlled binary conductance switching of a single-molecule junction. Nat Nanotechnol. Apr. 2009;4(4):230-4. doi:10.1038/nnano.2009.10. Epub Mar. 1, 2009.
Rief et al., Sequence-dependent mechanics of single DNA molecules. Nat Struct Biol. Apr. 1999;6(4):346-9.
Ritort, Single-molecule experiments in biological physics: methods and applications. J Phys Condens Matter. Aug. 16, 2006;18(32):R531-83. doi:10.1088/0953-8984/18/32/R01. Epub Jul. 25, 2006.
Rothemund, Folding DNA to create nanoscale shapes and patterns. Nature. Mar. 16, 2006;440(7082):297-302.
Sacca et al., DNA origami: the art of folding DNA. Angew Chem Int Ed Engl. Jan. 2, 2012;51(1):58-66. doi: 10.1002/anie.201105846. Epub Dec. 7, 2011.
Seeman, DNA in a material world. Nature. Jan. 23, 2003;421(6921):427-31.
Seeman, Nanomaterials based on DNA. Annu Rev Biochem. 2010;79:65-87. doi: 10.1146/annurev-biochem-060308-102244.
Shroff et al., Biocompatible force sensor with optical readout and dimensions of 6 nm3. Nano Lett. Jul. 2005;5(7):1509-14.
Shroff et al., Optical measurement of mechanical forces inside short DNA loops. Biophys J. Mar. 15, 2008;94(6):2179-86. Epub Dec. 7, 2007.
Smith et al., Overstretching B-DNA: the elastic response of individual double-stranded and single-stranded DNA molecules. Science. Feb. 9, 1996;271(5250):795-9.
Strunz et al., Dynamic force spectroscopy of single DNA molecules. Proc Natl Acad Sci U S A. Sep. 28, 1999;96(20):11277-82.
Svoboda et al., Direct observation of kinesin stepping by optical trapping interferometry. Nature. Oct. 21, 1993;365(6448):721-7.
Thorne, Electrophoretic separation of polyoma virus DNA from host cell DNA. Virology. Jun. 1966;29(2):234-9.
Thuring et al., A freeze-squeeze method for recovering long DNA from agarose gels. Anal Biochem. May 26, 1975;66(1):213-20.
Wiita et al., Force-dependent chemical kinetics of disulfide bond reduction observed with single-molecule techniques. Proc Natl Acad Sci U S A. May 9, 2006;103(19):7222-7. Epub Apr. 27, 2006.
Williams et al., Entropy and heat capacity of DNA melting from temperature dependence of single molecule stretching. Biophys J. Apr. 2001;80(4):1932-9.
Winfree et al., Design and self-assembly of two-dimensional DNA crystals. Nature. Aug. 6, 1998;394(6693):539-44.
Wong et al., The effect of integration time on fluctuation measurements: calibrating an optical trap in the presence of motion blur. Opt Express. Dec. 11, 2006;14(25):12517-31.
Zadeh et al., NUPACK: Analysis and design of nucleic acid systems. J Comput Chem. Jan. 15, 2011;32(1):170-3. doi: 10.1002/jcc.21596.

(56) References Cited

OTHER PUBLICATIONS

Zhang et al., Mechanoenzymatic cleavage of the ultralarge vascular protein, von Willebrand Factor. Science. Jun. 5, 2009;324(5932):1330-4.

Zheng et al., From molecular to macroscopic via the rational design of a self-assembled 3D DNA crystal. Nature. Sep. 3, 2009;461(7260):74-7. doi: 10.1038/nature08274.

* cited by examiner

SYSTEMS AND APPARATUS FOR DETECTING COMPOUNDS IN HUMAN BIOLOGICAL SAMPLES

RELATED APPLICATION

This Application is a national stage filing under 35 U.S.C. 371 of International Patent Application Serial No. PCT/US2017/023711, filed Mar. 23, 2017, entitled "SYSTEMS AND APPARATUS FOR DETECTING COMPOUNDS IN HUMAN BIOLOGICAL SAMPLES", which claims priority under 35 USC 119(e) to U.S. Provisional Application Ser. No. 62/311,977, filed Mar. 23, 2016, entitled "SYSTEMS AND APPARATUS FOR DETECTING COMPOUNDS IN HUMAN BIOLOGICAL SAMPLES". The entire contents of these applications is incorporated by reference herein in its entirety.

GOVERNMENT LICENSE RIGHTS

This invention was made with government support under GM119537 awarded by the National Institutes of Health. The government has certain rights in the invention.

BACKGROUND

Testing or screening of human biological samples such as serum or urine for a particular compound (e.g., protein analyte) in the sample facilitates identification of a particular medical condition for the human from which the sample is obtained. Some screening tests are performed in laboratories based on samples collected from patients at a medical clinic or hospital. An example of such a test is a test for cholesterol levels by analyzing a patient's blood sample. Other screening tests are prescribed by a physician or may be purchased over-the-counter for home use.

SUMMARY

Provided herein are descriptions of apparatus for analyzing human biological samples such as serum and urine for the presence of compounds (e.g., protein analytes) having particular binding activities to nucleic acid complexes. Apparatus in accordance with some embodiments include one or more of a collection device, a sample processing device, and an imaging device for providing an indication of whether a sample provided as input to the apparatus contains compounds indicative of a particular medical condition.

One aspect of this disclosure is directed to a point-of-care device configured to receive a human biological sample, process the biological sample using a gel electrophoresis technique, image the gel used for gel electrophoresis, and output an indication that a particular compound was detected in the input biological sample. In one aspect the point-of-care device is configured to communicate with a computing device such as a smartphone or tablet computer to provide the indication. In another aspect the indication is provided on the point-of-care device without connection to a separate computing device. In one aspect the point-of-care device is disposable.

One aspect of this disclosure is directed to a high-throughput device configured to receive multiple human biological samples, and to process the multiple biological samples using gel electrophoresis processes. The high-throughput device may include a display configured to display data corresponding to gel electrophoresis results.

One aspect of this disclosure is directed to an integrated device including a sample collection component, a processing component, and an imaging component. Integration of multiple components within a single device may enable for a lower cost and/or disposable detection system.

One aspect of this disclosure is directed to a collection device configured to collect a biological sample and provide a desired amount of the collected biological sample to a sample preparation chamber in which the biological sample is combined with a substance (e.g., a fluid) including nucleic acid complexes. In one aspect, the sample preparation chamber may also be configured to incubate the combined mixture for a particular amount of time.

One aspect of this disclosure is directed to a reader device configured to perform gel electrophoresis on a human biological sample that has been combined with a substance including nucleic acid complexes configured to bind with compounds in the human biological sample. In one aspect the reader device is portable and capable of being connected to an external power source. In another aspect the reader device is integrated with a sample collection device configured to receive the human biological sample.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Following below are more detailed descriptions of various concepts related to, and inventive embodiments of, methods and apparatus according to the present disclosure for analyzing biological samples. Examples of specific implementations and applications are provided primarily for illustrative purposes.

Testing or screening of human biological samples such as serum or urine for a particular compound (e.g., protein analyte) in the sample facilitates identification of a particular medical condition for the human from which the sample is obtained. For example, elevated levels of particular hormones or proteins detected in a urine sample may be used to predict stages of fertility including ovulation, fertilization, or implantation. Some screening tests are performed in laboratories based on samples collected from patients at a medical clinic or hospital. An example of such a test is a test for cholesterol levels by analyzing a patient's blood sample.

Other screening tests are prescribed by a physician or may be purchased over-the-counter for home use. An example of such a test is a home pregnancy test.

The inventors have recognized and appreciated that existing devices for testing or screening human biological samples may be improved by using measurement techniques that improve the sensitivity and/or accuracy of such devices. Some embodiments described herein relate to an improved screening device for analyzing human biological samples.

Figure 1:
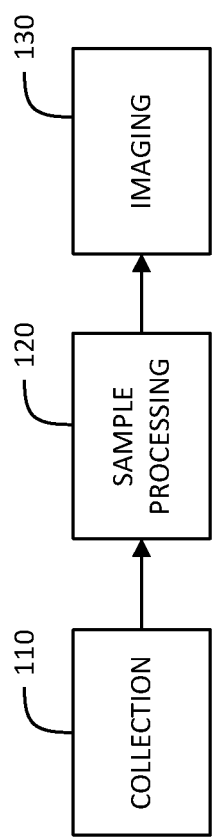
FIG. 1 is a schematic diagram of a components of an apparatus for analyzing human biological substances in accordance with some embodiments.

FIG. 1 schematically illustrates components of a biological sample analysis device in accordance with some embodiments. Collection device 110 is configured to collect a biological sample from a human. In some embodiments, the biological sample may be deposited directly onto a portion of collection device 110. In other embodiments, the biological sample may be deposited in a container separate from the collection device 110 and be drawn into collection device 110 using a capillary action, wicking action, or some other suitable technique. In yet other embodiments, collection device 110 may include a first portion comprising a larger collection receptacle for depositing a biological sample and a second portion comprising a smaller collection chamber connectable with the first portion. Examples of collection device 110 that may be used in accordance with some embodiments are described in more detail below in connection with FIGS. 2 and 3.

Collection device 110 transfers the collected sample to sample processing device 120, which processes the sample using a measurement technique for detecting a compound in the collected sample. In some embodiments described in more detail below, sample processing device 120 performs gel electrophoresis on the collected sample that has been combined with another substance, with the results of the gel electrophoresis technique being used to detect the presence/absence of a compound in the sample. Examples of sample processing devices that may be used in accordance with some embodiments are described in more detail below in connection with FIGS. 4, 6, and 7.

After processing the collected sample using sample processing device 120, an analysis of the processed sample performed by imaging device 130. In embodiments in which the sample is processed using gel electrophoresis, one or more images of the gel electrophoresis results may be captured using imaging device 130, and the captured image (s) may be used to detect the presence/absence of a compound in the sample. For example, substances input to a gel electrophoresis process migrate different distances along a gel electrophoresis track based on characteristics of the input substances. Accordingly, various components of the input substance may be inferred based on the distance that the substance migrates along a gel electrophoresis track in the presence of an applied electric field. Image(s) captured by imaging device 130 may be used to determine the distance that different input substances migrate along a track in sample processing device 120, thereby determining whether a particular compound is present/absent in the tested sample.

Figure 2:
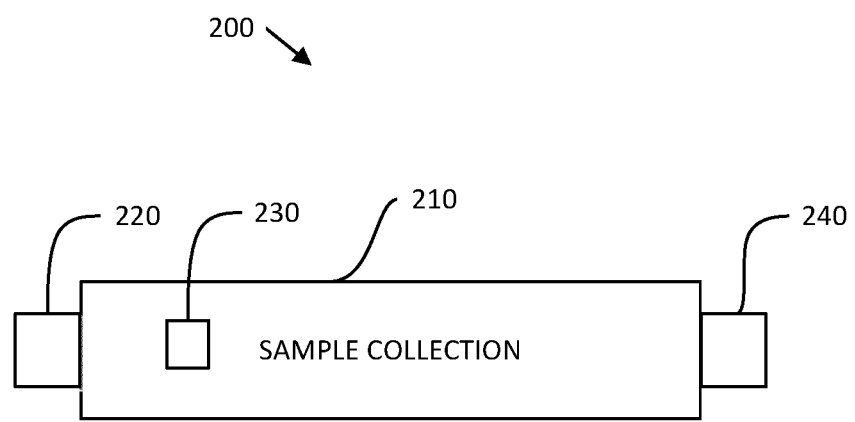
FIG. 2 shows an example of a sample collection device in accordance with some embodiments.

FIG. 2 illustrates an example of a collection stick device 200 as an example of collection device 110 that may be used in accordance with some embodiments. Collection device 200 includes a rigid body 210, which may be made from plastic or another suitable rigid material. Attached to body 210 is input port 220 arranged to receive a biological sample. For example, input port 220 may comprise a wicking material onto which a urine sample is deposited for testing. Use of a wicking material may be particularly advantageous if, for example, the biological sample is first deposited into a different receptacle (not shown) and is transferred to collection device 200 via input port 220. In some embodiments, in response to the placement of biological sample onto input port 220 at least a portion of the deposited biological sample is drawn into collection device 200. In addition to, or alternatively to including input port 220, some embodiments of collection device 200 include sample input window 230 onto which a biological sample may be deposited. For example, one or more drops of blood (or some other biological material) may be input to collection device 200 via sample input window 230 for testing.

In some embodiments, sample collection device 200 is configured to collect a biological sample for processing by one or more other devices without processing of the sample within the collection device. In other embodiments, collection device 200 is configured to perform at least some processing on a biological sample received by the collection device. For example, at least a portion of collection device collection device 200 may contain a substance that is combined with the input sample when received by the collection device. An example of such a substance is a fluid comprising nanoswitch molecules, described in more detail below, that interact with components of an input sample when combined in solution. The substance that is combined with the input sample may be stored in a receptacle within collection device and/or coated on a portion of collection device 200 such that when a sample is introduced to the collection device via an input port, the input sample and the substance are combined. In yet other embodiments, the substance combined with the input sample may be introduced via the same or a different input port of collection device 200. For example, the biological sample may be introduced via input port 220 and the substance to be combined may be introduced via sample input window 230 or both of the biological sample and the substance may be input to collection device 200 via sample input window 230.

In some embodiments, collection device 200 includes communications connector 240 configured to communicate information with an external device. For example, communications connector 240 may be a USB connector, a mini-USB connector, a IEEE 1394 connector, or some other suitable connector configured to exchange information with a computing device. The computing device, when connected, may perform additional processing and/or provide power to collection device 200 to perform gel electrophoresis or some other process that requires a power source to operate.

Figure 3:
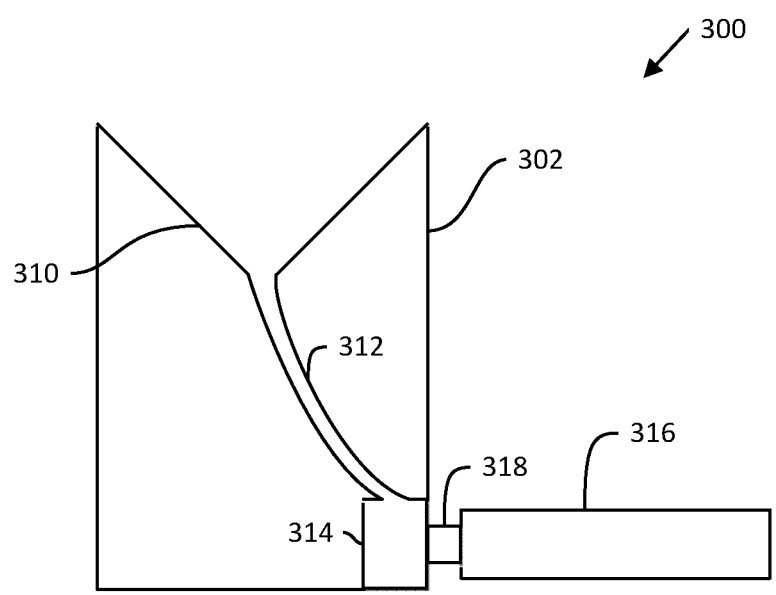
FIG. 3 shows an example of an alternate sample collection device in accordance with some embodiments.

The inventors have recognized that some measurement techniques used in accordance with some embodiments require only a small amount (e.g., 5-50 µL) of biological sample for processing, but collecting such a small amount of sample may present challenges. FIG. 3 illustrates a cup-based collection device 300 as an alternate embodiment of collection device 110. Collection device 300 includes a cup portion 302 that receives the biological sample as input and a connectable sample collection portion 316 that receives the sample from cup portion 302 for further processing. In some embodiments, collection portion 316 is substantially similar to collection device 200 described in connection with FIG. 2.

Cup portion 302 of collection device 300 includes a large opening 310 into which a biological sample (e.g., urine) may be input. The received biological sample is transferred to collection chamber 314 via channel 312 connecting the opening 310 and the collection chamber 314. Although opening 310 and channel 312 illustrated in FIG. 3 form a funnel-shaped configuration in which the biological sample flows into collection chamber 314, it should be appreciated that the sample input into opening 310 may be transferred to collection chamber 314 in any suitable way, at any suitable rate, and using any suitable configuration. In some embodiments, collection chamber 314 includes or is coated with a substance that is combined with an input sample introduced into chamber 314 via channel 312.

After collection of a portion of the biological sample in collection chamber 314, collection portion 316 may be coupled to collection chamber 314 to transfer at least a portion of the input sample (combined or not combined with another substance) to collection portion 316. For example, collection portion 316 may include an input port 318 comprising a wicking material that, when inserted into collection chamber draws at least some of the input sample into collection portion 316 for processing and/or transfer to another device for processing. To prevent the sample from exiting chamber 314 when input port 318 is not inserted into the chamber, chamber 314 may include a seal that may be broken by input port 318 and/or cup portion may include a removable cap portion (not shown) that covers an outlet of chamber 314 and can be removed to enable input port 318 to be inserted into chamber 314.

In FIG. 3, cup portion 302 and collection portion 316 are shown as separate components connectable to each other. In some embodiments, a miniaturized version of cup portion 302 is provided as an integral portion of collection portion 316. For example, a miniaturized cup portion 302 may be included directly below sample input window 230 of collection device 200 shown in FIG. 2. By including a miniaturized version of cup portion 302 within the collection device, flow of the input sample may controlled such that a desired amount of the sample is introduced into a chamber. In some embodiments, the chamber 314 may include or be coated with a substance, as discussed above, that when combined with the input sample prepares the sample for further processing, as discussed in further detail below.

Figure 4:
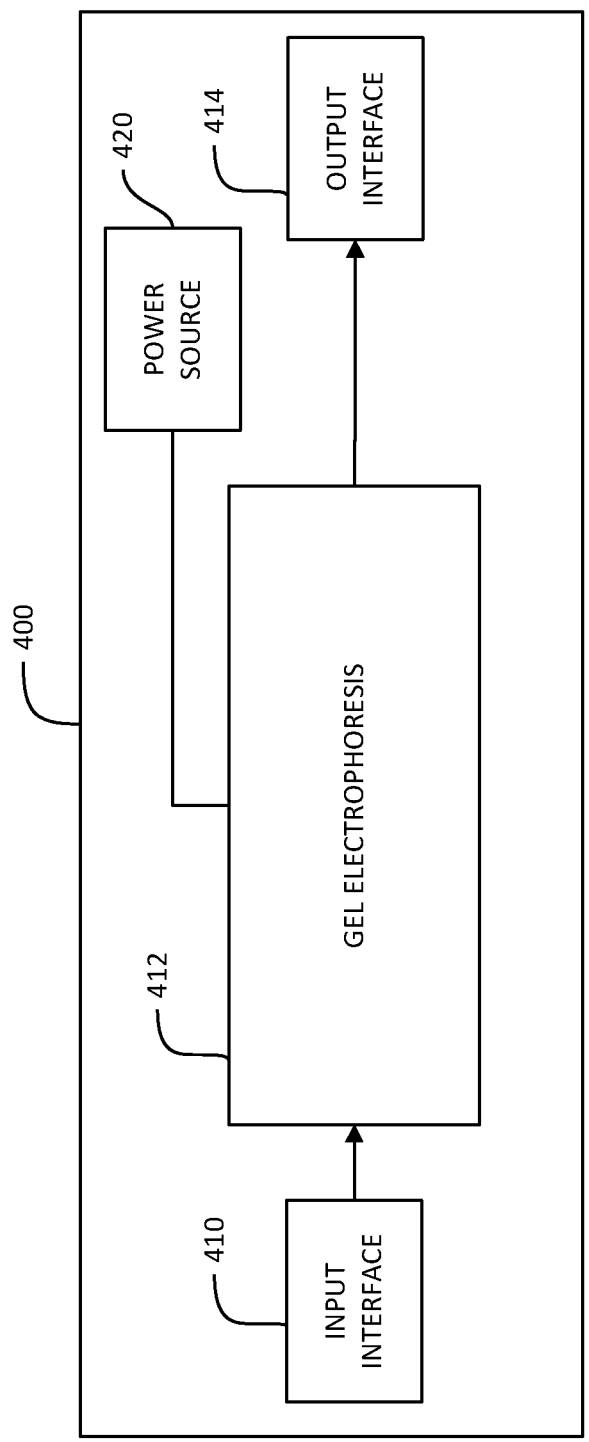
FIG. 4 is a schematic diagram of a sample processing device in accordance with some embodiments.

FIG. 4 schematically illustrates components of a sample processing or "reader" device 400, as an example of sample processing device 120. Reader device 400 includes input interface 410 that receives an input sample from a collection device 110 (e.g., collection device 200 or 300). In some embodiments, input interface 410 is implemented as a chamber or an absorbent material configured to absorb at least a portion of the input sample introduced into the input interface from a collection device. Input interface 410 may include or be coated with a substance that is combined with the input sample when introduced into the reader device 400 via input interface 410. For example, in some embodiments input interface includes a chamber that includes a fluid with nanoswitch molecules that, when combined with the input sample change some aspect of the nanoswitch molecules when a particular compound is present in the input sample, and the changed aspect is detectable using gel electrophoresis, as described in more detail below.

In some embodiments, after the sample is combined with the substance (e.g., a coating or fluid with nanoswitch molecules), the combination is incubated prior to processing the sample using gel electrophoresis. Accordingly, reader device 400 may include suitable components to enable the incubation process to proceed for a particular amount of time, as desired. For example, reader device 400 may include one or more additional substances (e.g., buffer substances) and/or timing electronics that measure an incubation time sufficient to determine that a necessary incubation time has taken place. In some embodiments, no timing electronics are included in reader device 400, and the user of the device may be responsible for determining that a suitable incubation period has passed prior to performing gel electrophoresis on the incubated sample. In some embodiments, any required incubation may be performed in a receptacle separate from reader device 400 and the incubated mixture may be provided to input interface 410 for processing by gel electrophoresis component 412.

As shown, reader device 400 includes gel electrophoresis component 412, which receives an input substance from input interface 410 and processes the input substance using a gel electrophoresis process. Gel electrophoresis is a technique by which molecules may be sorted based on how far the molecules migrate in a gel substrate in the presence of an applied electric field. Any suitable gel substrate including, but not limited to agarose and polyacrylamide, may be used. In accordance with some embodiments, particular markers in the input sample are detectable when compounds in the sample modify the morphology of nanoswitch molecules, with the change the morphology causing the nanoswitch molecules to more slowly or more quickly migrate along the gel substrate. A more detailed discussion of a nanoswitch molecule technique that may be used in accordance with some embodiments is discussed in more detail below.

As discussed above, gel electrophoresis operates by applying an electric field across a gel substrate such that molecules migrate from a negatively-charged cathode toward a positively-charged anode at different rates. Power used to create the electric filed may be provided by power source 420 included as a portion of reader device 400. For example, reader device 400 may include a battery configured to provide current to an anode and a cathode to generate an electric field for gel electrophoresis component 412. In some embodiments, reader device 400 does not include an onboard power source. In such embodiments, the electric field for gel electrophoresis may be generated based on current provide by a power source external to reader device 400. For example, power may be provided by inclusion on reader device 400 of an interface for receiving AC (e.g., a standard wall plug) or DC power. In some embodiments, reader device 400 includes a data communications interface (e.g., a USB interface) that provides power to the reader device 400 for performing gel electrophoresis.

Reader device 400 also includes an output interface 414 for outputting a result of the gel electrophoresis process. Output interface 414 may be implemented in any suitable way to enable data corresponding to the gel electrophoresis results to be output from reader device 400. As discussed in further detail below, in some embodiments, reader device 400 includes imaging components (not shown) configured to capture an image of the gel following electrophoresis, and the captured image may be output via output interface. In some embodiments, output interface comprises a transparent window in reader device 400 that enables an external imaging system (e.g., a cell phone/smartphone/tablet camera) to capture an image of the gel following electrophoresis. An example of an external imaging system that may be used in accordance with some embodiments is described in more detail below.

Figure 5:
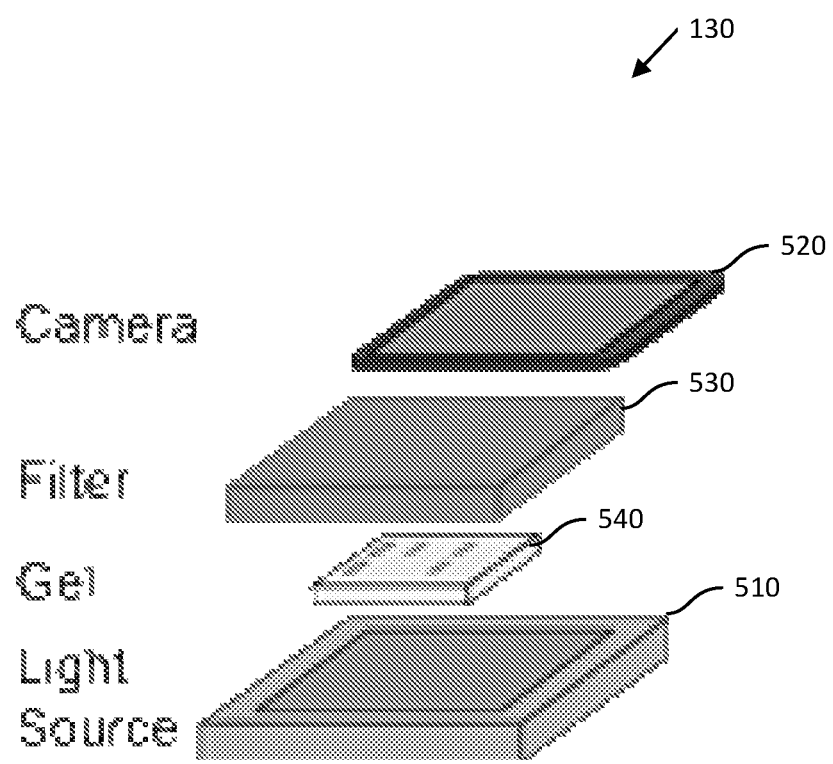
FIG. 5 is a schematic diagram of an imaging device in accordance with some embodiments.

FIG. 5 shows an example of an imaging device 130 that may be used to capture an image of a gel following electrophoresis in accordance with some embodiments. The imaging device includes a light source 510 configured to illuminate gel 540 and a recording device 520 (e.g., a camera) provided on an opposite side of gel 540 to capture an image of gel 540. Although shown as being on opposite sides of gel 540, in some embodiments both the light source 510 and the recording device 520 may be provided on the same side of gel 540 for imaging. Any suitable light source 510 may be used to illuminate gel 540. In some embodiments, a light source integral in a portable or mobile (e.g., cell phone/smartphone) camera may be used to illuminate the gel 540 for imaging. For example, some smartphones and tablet computers include an LED-based camera flash that can be activated to illuminate gel 540. In other embodiments, light source 510 corresponds to a standalone light source, such as a light box, which is separate from recording device 520. Although the illustrative light sources described above provide radiation in the visible spectrum, it should be appreciated that radiation in any suitable spectrum including, but not limited to radiation in the ultraviolet, infrared, or near-infrared spectra may alternatively be used.

As shown, a filter 530 may be used in some embodiments to create a filtered image using camera 520. For example, light source 510 may be configured to cause compounds on gel 540 to emit photons having a particular wavelength. A filter 530 may be arranged between the gel 540 and the recording device 520 to filter the emitted radiation to improve the signal to noise ratio (SNR) of the recording device 520.

Figure 6:
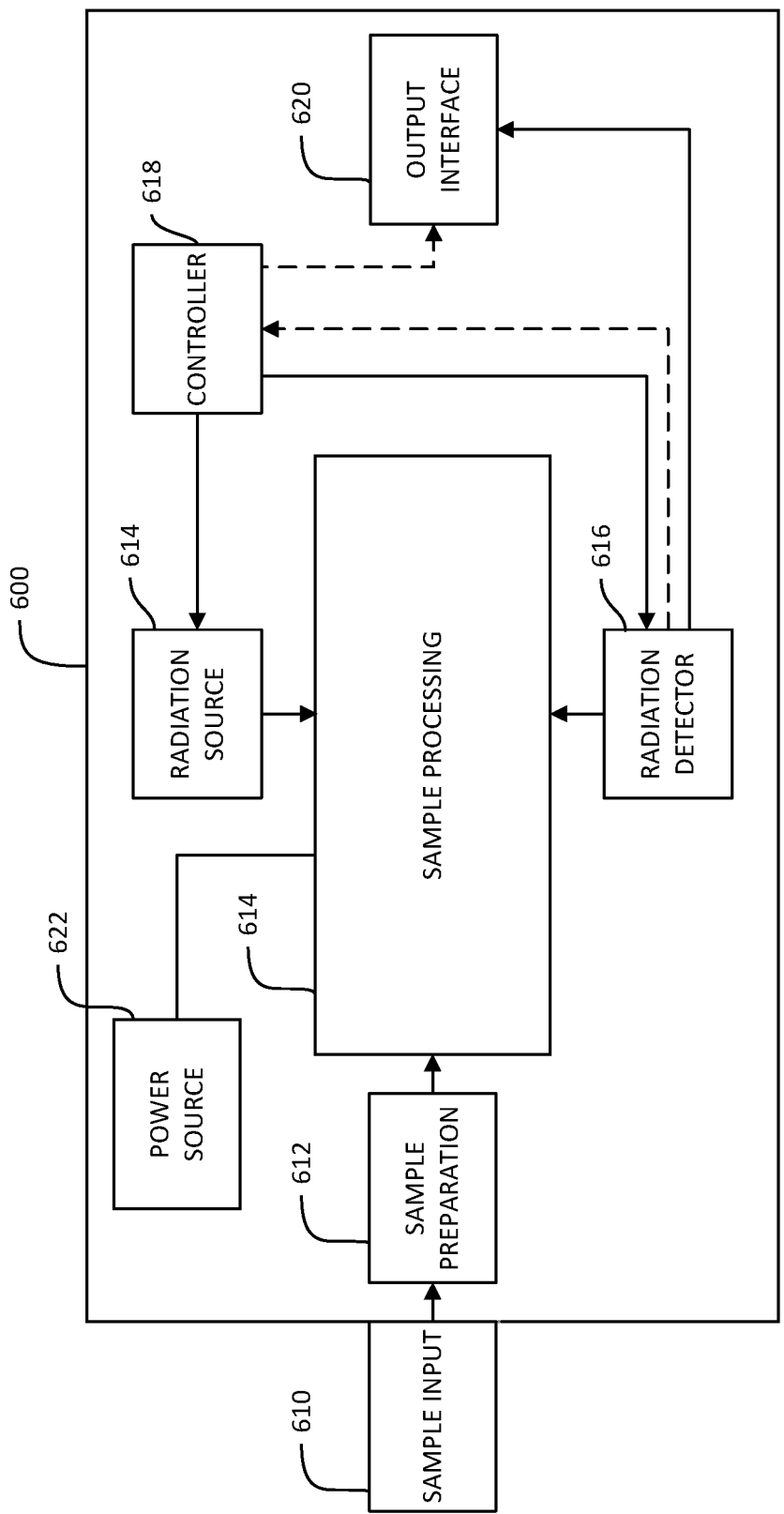
FIG. 6 is a schematic diagram of an integrated device in accordance with some embodiments.
Figure 7:
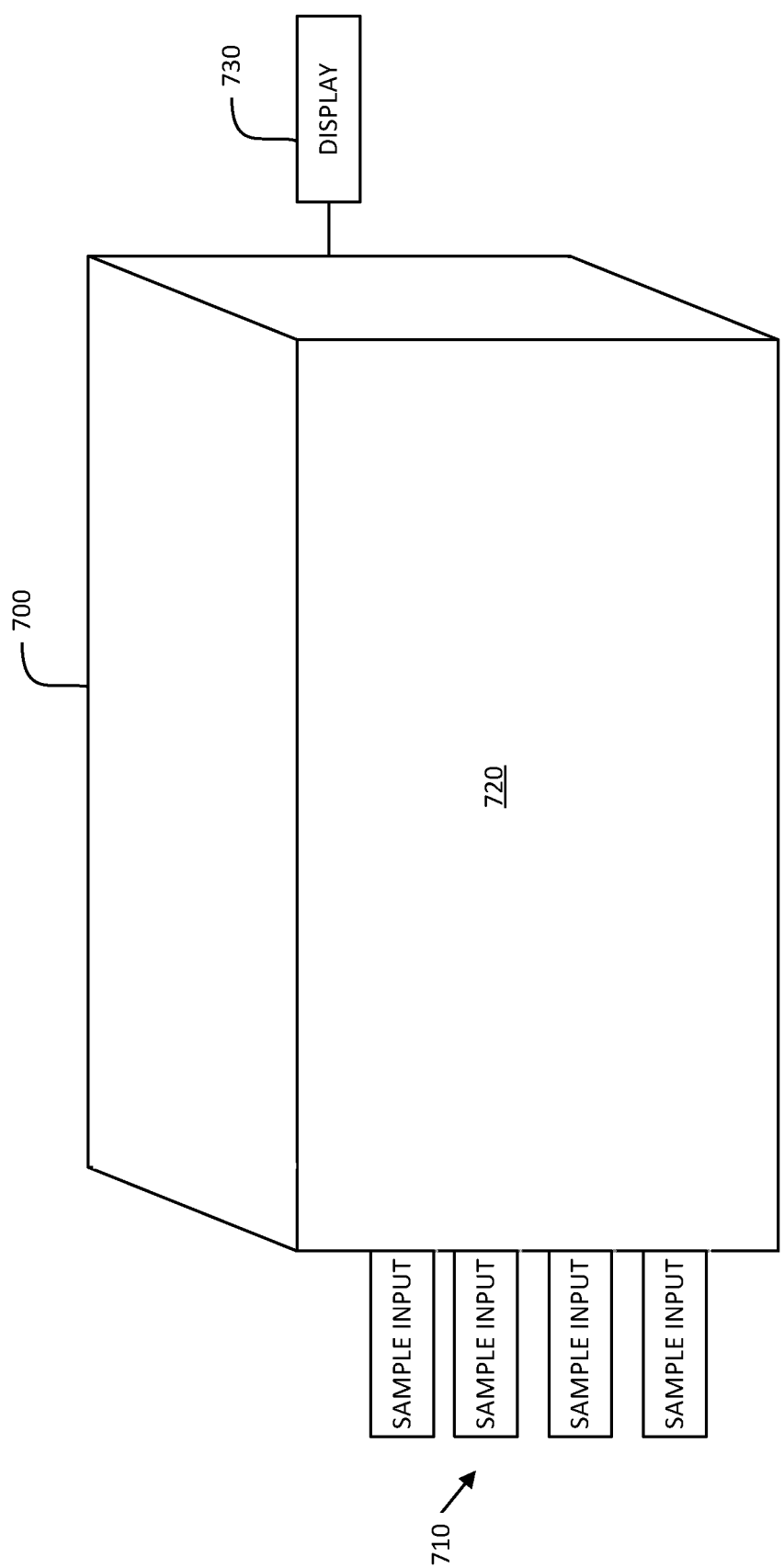
FIG. 7 is a schematic diagram of a high-throughput device in accordance with some embodiments.

The inventors have recognized that apparatus embodying applications of the inventive concepts described herein may be used in different environments and by different users. Depending on the environment in which the apparatus is used, more or less integration of the collection, sample processing, and imaging devices may be needed or desired. In some embodiments, an example of which is shown in FIG. 6, most or all of collection, sample processing, and imaging components are integrated within a single integrated device 600. The integrated device may be packaged as, for example, an ovulation or pregnancy test kit that may prescribed or purchased over the counter for in home use. In other embodiments, an example of which is shown in FIG. 7, the apparatus may be configured as a high-throughput screening apparatus 700 for use in a laboratory or clinic environment.

As shown in FIG. 6, integrated device 600 includes a sample input interface 610 configured to receive a biological sample such as urine or serum. Non-limiting examples of sample input interfaces 610 are described above in connection with FIGS. 2 and 3. The sample received via sample input interface 610 is provided to sample preparation component 612 prior to gel electrophoresis. For example, as discussed above, some biological samples may be combined with other substances (e.g., nanoswitch molecules, dyes) and/or incubated for a particular amount of time prior to performing analysis on the sample. Sample preparation component 612 may be implemented as a separate chamber or substrate within integrated device 600 or may be integrated with sample input interface 610.

Integrated device 600 includes sample processing component 614 configured to process a human biological sample after preparation by sample preparation component 612. As discussed above in connection with FIG. 4, some embodiments are configured to perform gel electrophoresis on biological samples. Accordingly, sample processing component 614 may be configured to perform gel electrophoresis. Integrated device 622 includes a power source 622 configured to provide an electric field necessary to perform gel electrophoresis. Power source 622 may be provided as a battery or some other power source within integrated device 600 or power may be provided from a power source external to integrated device 600 such as via a data communications port or an AC power interface.

Integrated device 600 also includes imaging components incorporated within the device. As shown, integrated device 600 includes a radiation source 614 and a radiation detector 616 arranged to image at least a portion of the gel used in sample processing section 614. In some embodiments, radiation source may comprise a single light emitting diode (LED) configured to illuminate the gel. In other embodiments, a small array of LEDs or other illumination sources may be used as radiation source 614 to illuminate the gel for imaging. Any suitable type of radiation source 614 including, but not limited to an ultraviolet radiation source, a visible light source, and an infrared light source, may be used. Radiation detector 616 is arranged relative to radiation source 614 and the gel included as a portion of sample processing component 614 to capture an image of the gel. In some embodiments, radiation detector 616 may include a single photodetector such as a photodiode configured to record a number of photons emitted from the imaged gel in response to illumination by radiation source 614. In other embodiments, radiation detector comprises a 1-dimensional or 2-dimensional array of photodetector elements arranged to capture an image of the gel. Use of a single LED light source and a single photodetector may facilitate implementation of a reduced cost disposable point-of-care device.

In one embodiment, radiation source 614 and radiation detector 616 are arranged relative to the gel to capture an image of a line perpendicular to the migration direction along the gel. During operation some molecules may migrate past the line being imaged resulting in detection of particular markers in the input sample. In such an embodiment, the molecules migrating through the gel may be analogous to objects moving on a conveyor belt past a stationary imaging source providing line images perpendicular to moving direction of the conveyor belt.

Radiation source 614 and radiation detector 616 may be controlled by a controller 618 included in integrated device 600 to capture an image of the gel used within sample processing component 614. Controller 618 may be implemented as a programmable microprocessor, an application-specific integrated circuit ASIC, a field programmable gate array (FPGA), or any other suitable control circuitry. In some embodiments, integrated device 600 may include a data communications interface (e.g., a USB interface) that, when connected to a computing device, enables controller 618 to be programmed to perform specific functions. In other embodiments, controller 618 is implemented as dedicated hardware circuitry. Such dedicated hardware circuitry may provide for a lower-cost disposable point-of-care device.

As shown, the output of radiation detector 616 is provided to output interface 620. Optionally, the output of radiation detector 616 may be provided to controller 618 for further processing prior to being provided to output interface 620, as shown by the dashed line path in FIG. 6. In the optional (dashed line) output path, any suitable processing (e.g., data compression, averaging, reconstruction, combining) may be provided by controller 618 prior to outputting the recorded data, and aspects are not limited in this respect.

In some embodiments, output interface 620 is configured to output an image captured by radiation detector 616. The image may be processed by a computing device (e.g., a smartphone or tablet computer) into which the integrated device 600 is in communication with. In other embodiments, output interface 620 is configured to output an indication of the presence/absence of a particular compound in the input sample in a manner similar to a conventional over-the-counter pregnancy test. For example, the indication may be presented as a symbol, icon, or other marking on the portable test. In some embodiments, one of multiple fertility states (e.g., ovulating, fertilized, implanted) may be detected by integrated device 600 and an output of the detected fertility state may be output by output interface 620.

FIG. 7 shows a high-throughput device that may be used in a laboratory or a clinical facility in which multiple input samples may be processed in parallel to detect compounds in human biological samples. Device 700 includes multiple sample inputs 710 for transferring input samples to processing component 720 of device 700. Processing component 720 may include a plurality of gel electrophoresis tracks along which a prepared sample may migrate in the presence of an electric field, as discussed above. Device 700 also includes a display 730 configured to display data associated with processed samples. Any suitable data including, but not limited to, an image of one or more gels included in processing component 720 may be displayed on display 730.

Figure 8:
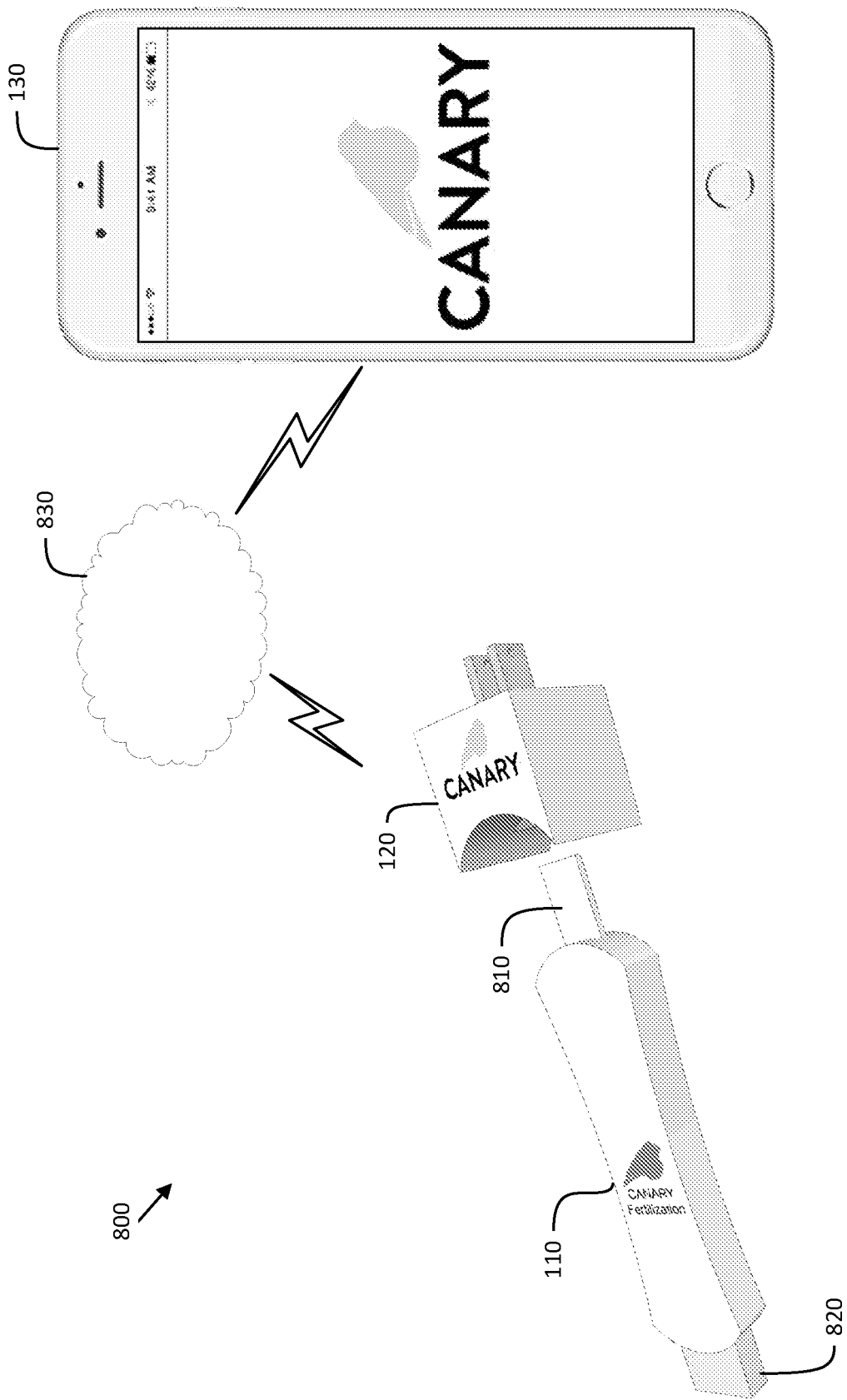
FIG. 8 is an illustration of a biological sample analysis device in accordance with some embodiments.

FIG. 8 schematically illustrates components of a system 800 for processing human biological samples in accordance with some embodiments. Collection device 110 includes a sample collection portion 810 for collecting a sample and a data communications interface 820 for communicating with a computing device. Reader device 120 is configured to receive power to generate an electric field for performing gel electrophoresis (not shown). Imaging device 130 implemented as a smartphone may be used to capture an image of the results of the gel electrophoresis performed by reader device 120. Alternatively imaging of the gel may be implemented as a portion of reader device 120, as described above. Data output from reader device and/or imaging device 130 may be transferred via one or more networks to a cloud-based resource 830 for storage and/or processing. One or more wired or wireless connections between components of system 800 and cloud-based resource 830 may be used, and aspects are not limited in this respect. Data processed and/or stored by cloud-based resource 830 may be downloaded to an application executing on a computing device (e.g., a smartphone) to provide an indication of the test results to a user. The computing device may interact with the cloud-based resource in any suitable way, and aspects are not limited in this respect.

Non-Limiting Technique for Preparing a Sample for Gel Electrophoresis

Nanoswitches Generally

The nanoswitches of this disclosure minimally comprise a scaffold or backbone nucleic acid comprising one or more, and typically two or more binding partners. The scaffold nucleic acid may be of any length sufficient to allow association (i.e., binding) and dissociation (i.e., unbinding) of binding partners to occur, to be detected, and to be distinguished from other events. In some instances, the scaffold nucleic acid is at least 1000 nucleotides in length, and it may be as long as 20,000 nucleotides in length (or it may be longer). The scaffold nucleic acid may therefore be 1000-20,000 nucleotides in length, 2000-15,000 nucleotides in length, 5000-12,000 in length, or any range therebetween. The scaffold may be a naturally occurring nucleic acid (e.g., M13 scaffolds such as M13mp18). M13 scaffolds are disclosed by Rothemund 2006 Nature 440:297-302, the teachings of which are incorporated by reference herein. The scaffold nucleic acid may be lambda DNA, in other embodiments. The scaffold nucleic acid may also be non-naturally occurring nucleic acids such as polymerase chain reaction (PCR)-generated nucleic acids, rolling circle amplification (RCA)-generated nucleic acids, etc.

In some embodiments, the binding partners are positioned along the scaffold nucleic acid to yield loops and thus length changes that are detectable. These may include loops that are about 40-100 base pairs, or about 100-1000 base pairs, or about 500-5000 base pairs. The scaffold may be partially or fully single-stranded or partially or fully double-stranded. The complex may comprise varying lengths of double-stranded regions.

The scaffold nucleic acid may comprise DNA, RNA, DNA analogs, RNA analogs, or a combination thereof. In some instances, the binding partners are conjugated to a scaffold nucleic acid via hybridization of oligonucleotides to the scaffold, wherein such oligonucleotides are themselves conjugated to a binding partner. In some instances, the scaffold nucleic acid is a DNA.

In some instances, then the scaffold nucleic acid may be hybridized to one, two or more, including a plurality, of oligonucleotides. Each of the plurality of oligonucleotides may hybridize to the scaffold nucleic acid in a sequence-specific and non-overlapping manner (i.e., each oligonucleotide hybridizes to a distinct sequence in the scaffold).

The number of oligonucleotides hybridized to a particular scaffold may vary depending on the application. Accordingly, there may be 2 or more oligonucleotides hybridized to the scaffold, including 3, 4, 5, 6, 7, 8, 9, 10, 20, 30, 40, 50, 60, 70, 80, 90, 100, 200, 300, 400, 500, 600, 700, 800, 900, or 1000 or more oligonucleotides.

In some instances, some oligonucleotides hybridized to the scaffold nucleic acid will be unmodified. Unmodified oligonucleotides include oligonucleotides that are not linked to binding partners such as binding partners being tested (e.g., an antibody or an antigen). In other instances, some or all the oligonucleotides hybridized to the scaffold may be modified. Modified oligonucleotides include those that are linked to binding partners being tested (e.g., a receptor and/or its ligand, an antibody and/or its antigen, etc.). Modified oligonucleotides may also include those that are modified and thus used to immobilize the nanoswitch to a solid support such as but not limited to a bead. Such modified oligonucleotides including biotinylated oligonucleotides. Modified oligonucleotides may be referred to herein as "variable" oligonucleotides since these oligonucleotides may be modified by linking to a variety of binding partners depending on the method of use.

Regions comprising scaffold hybridized to modified oligonucleotides may be referred to herein as "variable" regions and the remaining scaffold regions may be referred to as "fixed" regions.

The scaffold-binding partner construct may be made in a number of ways including through nicking of a double stranded nucleic acid to which binding partners are conjugated (to one strand), or by hybridization of one or more oligonucleotides to the scaffold, as described herein in greater detail.

In other instances, the binding partners may be conjugated to the scaffold nucleic acid itself rather than to an oligonucleotide that is hybridized to the scaffold.

The spacing of binding partners, and thus in some instances of the modified (or variable) oligonucleotides, along the length of the scaffold nucleic acid may vary. In some embodiments, the nanoswitch may comprise two, three or four binding partners, and thus in some embodiments variable regions (e.g., two or three or four modified oligonucleotides). As an example, a nucleic acid nanoswitch may comprise two internal modified oligonucleotides. The modified oligonucleotides internal to the nanoswitch may be linked individually to members of a binding pair (i.e., each of the two oligonucleotides is linked to a member of the binding pair such that the nanoswitch comprises the binding pair, with each member of the pair on a different oligonucleotide). The internal modified oligonucleotides may be symmetrically or quasi-symmetrically located around the center of the scaffold. In other words, they may be positioned equi-distant from the center of the scaffold.

The distance between the binding pair members may be 300 base pairs, 200 base pairs, 150 base pairs, 100 base pairs, 80 base pairs, 60 base pairs, and 40 base pairs.

Importantly, the distance between the binding partners will be used to distinguish association and dissociation between binding partners linked to the nanoswitches. This is because when the binding partners are associated with each other, a loop will be formed comprising the nucleic acid sequence that exists between the binding partners. When the binding partners are not associated to each other (i.e., unbound), then the loop does not form and the complex length is different (i.e., longer). The nanoswitch configuration can be determined by analyzing the migration of the nanoswitch through a matrix such as a gel in a gel electrophoretic system. The unbound, linear form travels more rapidly than does the bound, looped form. Thus, presence of an analyte of interest, to which the binding partners on a single nanoswitch bind, will trigger the formation of a bound and looped nanoswitch. The bound, looped nanoswitch will be distinguished from its unbound, linear counterpart based on the difference in their migration distances through a gel or other pore-containing matrix.

It is to be understood that several variations on the nucleic acid nanoswitches described herein. Typically, these variations all commonly comprise a nucleic acid nanoswitches having two or more binding partners. The binding partners typically have binding specificity for a common analyte. Several of the methods rely on the association and/or dissociation of binding partners. A change in conformation of the nanoswitch (e.g., from an open to a closed conformation) provides information about the presence of the analyte. The binding partners may be non-covalently or covalently bound to the scaffold.

In another variation, the nucleic acid complex comprises two binding partners having binding specificity for a common analyte. The binding partners are physically separate and thus spaced apart from each other (when not bound to the common analyte). When bound to the common analyte, the nucleic acid nanoswitch assumes a looped (or closed or bound) conformation having a different formation and thus a different "apparent" length (as for example measured using migration through a gel electrophoresis system), compared to the nucleic acid nanoswitch in an open (or unbound) conformation.

The invention further contemplates that a nucleic nanoswitches may comprise more than two conjugated binding partners. The number of binding partners may be 2, 4, or more. In some embodiments, pairs of binding partners are provided, with each pair having binding specificity for a particular analyte. A single nanoswitch may comprise a binding pair for a first analyte, which may be a test analyte, and a second binding pair for a second analyte, which may be a control analyte. In this way, the nanoswitch may have a control reading as well as a test reading. For example, if the nanoswitch is used to measure a marker of ovulation or pregnancy, then a first binding pair may bind to such marker and a second binding pair may bind to a control protein or other moiety that will always be present in the sample being tested (e.g., the urine) in order to establish to the end user that a sufficient quantity of sample was applied to the system. The location or arrangement of the binding partners may vary and may include serially positioned binding pairs or nested binding pairs, or combinations thereof. As an example, assume that A1 and A2 are a binding pair (e.g., first and second binding partners) and B1 and B2 are a different binding pair (e.g., third and fourth binding partners), then these may be arranged as 5'-A1-A2-B1-B2-3', or they may be arranged as 5'-A1-B1-B2-A2-3'. Alternatively, the test and control analytes may be assayed using different nanoswitches that are nevertheless still run through the same gel system.

The nanoswitches comprise binding partners such as for example an antibody or an antigen. The linkage between the nucleic acid and the binding partner may be covalent or non-covalent depending on the strength of binding required for a particular application. They may be generated by first incorporating a reactive group (or moiety) into the nucleic acid (or into an oligonucleotide hybridized to the nucleic acid), and then reacting this group (or moiety) with the binding partner of interest which may or may not be modified itself. Suitable reactive groups are known in the art. Examples of reactive groups that can covalently conjugate to other reactive groups (leading to an irreversible conjugation) include but are not limited to amine groups (which react to, for example, esters to produce amides), carboxylic acids, amides, carbonyls (such as aldehydes, ketones, acyl chlorides, carboxylic acids, esters and amides) and alcohols. Those of ordinary skill in the art will be familiar with other "covalent" reactive groups. Examples of reactive groups that non-covalently conjugate to other molecules (leading to a reversible conjugation) include biotin and avidin or streptavidin reactive groups (which react with each other), antibody (or antibody fragment) reactive groups and antigens, receptors and receptor ligands, aptamers and aptamer ligands, nucleic acids and their complements, and the like. Virtually any reactive group is amenable to the methods of the invention, provided it participates in an interaction of sufficient affinity to prevent dissociation of the binding partner from the nucleic acid nanoswitch.

It is to be understood that the scaffold nucleic acid and if used the oligonucleotides may be DNA or RNA in nature, or some combination thereof, or some analog or derivative thereof. The term nucleic acid refers to a polymeric form of nucleotides of any length, including deoxyribonucleotides, ribonucleotides, or analogs thereof. In some embodiments, the nucleic acids will be DNA in nature, and may optionally comprise modifications at their 5' end and/or their 3' end.

In some embodiments, the binding partners may include without limitation antibodies (or antibody fragments) and antigens, receptors and ligands, aptamers and aptamer receptors, nucleic acids and their complements, and the like. This list is not intended to be limited or exhaustive and other binding partners will be apparent and may be used in conjunction with the nanoswitches described herein.

Various aspects of embodiments may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, embodiments may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

The phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having thus described at least one illustrative embodiment of the invention, various alterations, modifications, and improvements will readily occur to those skilled in the art. Such alterations, modifications, and improvements are intended to be within the spirit and scope of the invention. Accordingly, the foregoing description is by way of example only and is not intended as limiting.

What is claimed is:

1. A diagnostic device configured to perform analysis of a human biological sample, the diagnostic device comprising:
   an input interface configured to receive the human biological sample from a user, wherein the input interface comprises a wicking material configured to provide the received human biological sample to sample processing machinery;
   the sample processing machinery configured to perform a gel electrophoresis process on a mixture including the received human biological sample combined with a plurality of nucleic acid nanoswitch molecules, wherein the plurality of nucleic acid nanoswitch molecules are configured to bind to at least one compound in the human biological sample, when present; and
   an output interface configured to output a gel electrophoresis result based on the gel electrophoresis process performed by the sample processing machinery.

2. The diagnostic device of claim 1, wherein the sample processing machinery comprises a chamber that includes the plurality of nucleic acid nanoswitch molecules wherein the mixture is formed in the chamber when the human biological sample is introduced into the chamber.

3. The diagnostic device of claim 2, wherein the chamber includes a fluid comprising the plurality of nucleic acid nanoswitch molecules.

4. The diagnostic device of claim 2, wherein the chamber is coated with a substance that includes the plurality of nucleic acid nanoswitch molecules.

5. The diagnostic device of claim 1, wherein the input interface is configured to connect to a container to receive the human biological sample and/or the mixture.

6. The diagnostic device of claim 1, wherein the input interface comprises a sample collection chamber.

7. The diagnostic device of claim 1, wherein the sample processing machinery further comprises a gel substrate and power source configured to provide an electric field across the gel substrate to perform the gel electrophoresis process.

8. The diagnostic device of claim 1, wherein the output interface comprises a transparent window that enables viewing of the gel electrophoresis result through the window.

9. The diagnostic device of claim 1, wherein the output interface comprises a data communications interface configured to output data corresponding to the gel electrophoresis result to a computing device.

10. The diagnostic device of claim 9, wherein the computing device comprises a cellular phone, a smartphone, or a tablet computer.

11. The diagnostic device of claim 9, wherein the computing device comprises at least one network-connected computer, and wherein the output interface is configured to output the data corresponding to the gel electrophoresis result to the at least one network-connected computer via one or more networks.

12. The diagnostic device of claim 1, wherein the output interface comprises an indicator provided on the device, wherein the indicator is configured to indicate the gel electrophoresis result to the user.

13. The diagnostic device of claim 1, further comprising imaging components integrated within the diagnostic device, wherein the imaging components are configured to capture an image of the gel electrophoresis result.

14. The diagnostic device of claim 13, wherein the imaging components include at least one radiation source and at least one radiation detector.

15. The diagnostic device of claim 14, wherein the imaging components further include at least one filter arranged to filter photons detected by the at least one radiation detector.

16. The diagnostic device of claim 13, wherein the output interface is configured to output the image captured by the imaging components.

17. The diagnostic device of claim 13, further comprising at least one controller programmed to control the imaging components to capture the image of the gel electrophoresis result.

18. A diagnostic system, comprising:
   a sample collection device configured to receive a human biological sample, wherein the sample collection device comprises a wicking material;
   a sample processing device configured to perform a gel electrophoresis process on the human biological sample received by the sample processing device via the wicking material of the sample collection device; and
   an imaging device configured to capture an image of a gel electrophoresis result produced by the gel electrophoresis process.

19. A high-throughput sample analyzer, comprising:
   an input interface configured to receive a plurality of human biological samples, wherein the input interface comprises wicking material configured to provide the plurality of received human biological samples to sample processing machinery;
   the sample processing machinery configured to perform a gel electrophoresis process for each of the received plurality of human biological samples, wherein the sample processing machinery includes a plurality of gel electrophoresis tracks, each of which is configured to interface with a mixture including one of the received human biological samples combined with a plurality of nucleic acid nanoswitch molecules, wherein the plurality of nucleic acid nanoswitch molecules are configured to bind to at least one compound in the human biological sample, when present; and
   an output interface configured to output a gel electrophoresis result for each of the plurality of gel electrophoresis tracks based on the gel electrophoresis process performed by the sample processing machinery.

* * * * *